United States Patent

Johansson et al.

[11] Patent Number: 5,170,419
[45] Date of Patent: Dec. 8, 1992

[54] X-RAY DIAGNOSTICS APPARATUS FOR MAMMOGRAPHY EXAMINATIONS

[75] Inventors: Per Johansson, Kungsaengen; Stefan Thunberg, Stockholm, both of Sweden

[73] Assignee: Siemens Aktiengesellschaft, Munich, Fed. Rep. of Germany

[21] Appl. No.: 863,049

[22] Filed: Apr. 3, 1992

[51] Int. Cl.$^5$ .............................. A61B 6/04
[52] U.S. Cl. ........................ 378/37; 378/181
[58] Field of Search .................. 378/37, 181

[56] References Cited

U.S. PATENT DOCUMENTS 4,394,771 7/1983 Charrier .
4,578,801 3/1986 Oliver .
4,613,982 9/1986 Dornheim et al. .
4,879,736 11/1989 Bergman et al. .

Primary Examiner—Craig E. Church

[57] ABSTRACT

An x-ray diagnostics apparatus for mammography examinations has an x-ray tube which is rotatable, via a horizontal shaft, around a bearing mounted in a stand, and having at least two cassette holders which can selectively individually be brought to an exposure position. The cassette holders are pivotable around the horizontal shaft so that when one cassette holder is situated in the exposure position, the other cassette holder is in a standby position. In order to make the apparatus relatively small and easily manipulable, the rotational axis of the horizontal shaft is disposed in approximate axial alignment with the middle of the examination subject, and the cassette holders are secured in a mount which is rotatably attached to the horizontal shaft, so that the standby position for each cassette holder is behind the x-ray tube, as seen by the examination subject. Rotation of the mount around the shaft is such that the cassette holders have approximately the same spacing from the rotational axis of the shaft when they are respectively situated in the exposure position.

16 Claims, 2 Drawing Sheets

X-RAY DIAGNOSTICS APPARATUS FOR MAMMOGRAPHY EXAMINATIONS

BACKGROUND OF THE INVENTION

1. Field of the Invention

The present invention is directed to an x-ray diagnostics apparatus of the type suitable for mammography examinations, and in particular to such an apparatus having at least two cassette holders which are movable so that when one cassette holder is in an exposure position, the other cassette holder is in a standby position.

2. Description of the Prior Art

An x-ray diagnostics apparatus for mammography examinations is disclosed in German OS 33 19 622 having an x-ray tube which, via a horizontal shaft is rotatable around a bearing arranged in a stand. Two cassette holders are provided which are pivotable around the horizontal shaft so that one cassette holder at a time can be brought to an exposure position, while the other cassette holder is situated in a standby position. The apparatus disclosed in German OS 33 19 622 has cassette holders for x-ray film cassettes of respectively different sizes. The holders are attached to a mount which is pivotable around a horizontal shaft, the horizontal shaft being disposed approximately between the x-ray tube and the image plane. This permits the mount to be fashioned so that the cassette holder in the standby position is situated above the x-ray tube. The mount together with the cassette holders form a U-shape, which is relatively large and is therefore rather difficult to maneuver when changing the position of a cassette holder from the exposure position to the standby position. This results in a rather clumsy impression of the unit arising on the part of the patient.

SUMMARY OF THE INVENTION

It is an object of the present invention to provide an x-ray diagnostics apparatus of the type having a horizontal shaft to which the x-ray tube is mounted, and around which at least two x-ray film cassette holders are pivotable between an exposure position and a standby position, wherein the x-ray tube can maintain its vertical position between successive exposures and the patient can remain standing at the unit during a cassette change.

It is a further object of the present invention to provide such an apparatus wherein the structure for permitting the cassette holders to be moved between the exposure position and the standby position is relatively small and easy to manipulate.

The above and other objects are achieved in accordance with the principles of the present invention in an x-ray apparatus for mammography exposures wherein the rotational axis of the horizontal shaft is disposed in substantially axial alignment with the middle of the examination subject, and wherein the cassette holders are secured in a mount which is rotatably attached to the horizontal shaft so that when one cassette holder is brought into the exposure position, the other cassette holder will be disposed in a standby position behind the x-ray tube, as seen by the examination subject. The x-ray tube has a front which faces the examination subject when the subject is standing in an examination position. A rear of the unit faces away from the patient, and this is the region referred to as "behind" the x-ray tube.

Rotation of the mount around the horizontal shaft ensues such that the cassette holders each have approximately the same spacing from the rotational axis of the horizontal shaft when they are respectively situated in the exposure position. An x-ray diagnostics apparatus of this type having a shaft for rotation of the x-ray tube with a rotational center approximately coinciding with the middle of the examination subject is shown, but is not described, in Swedish Application 9100362-4. The position-changing arrangement for the cassette holders, as disclosed herein, is particularly suited for an x-ray diagnostics apparatus of this type. Because the cassette holders, in their standby position, are situated in the space between the x-ray tube and the stand, the cassette holders are not in the way of the attending personnel. Moreover, an observer is given the impression of an elegant design. As a result of this structure, the position-changing arrangement can be kept small and is thereby easy to manipulate.

In an embodiment of the invention, the holder is attached to the horizontal shaft at an angle of approximately 45°. As a result, the cassette holders, when viewed in profile, can be attached to the mount so that they form an angle relative to each other of 90°.

In another embodiment of the invention, the mount can carry three cassette holders respectively disposed at angular spacings of 120°. The third cassette holder may, for example, be a digital plate employed during screening. As a result of the angular spacing between the cassette holders, the further cassette holders in their respective standby positions will not be in the way when the third cassette holder is in the exposure position.

In another embodiment of the invention, a bearing housing is attached to the horizontal shaft, with a bearing plate attached to the bearing housing at an angle of approximately 45° relative to the shaft, with the cassette mount being attached to the bearing plate. This results in an extremely simple structure for fastening the mount to the shaft.

It is preferred for a structurally simple fashioning of the invention that the bearing housing be provided with at least one flange to which the bearing plate is secured. This structure achieves a simple and stable connection between the bearing housing and the bearing plate.

In another embodiment of the invention, the mount is attached so as to be rotatable around the bearing plate with a ring, the ring being provided with a cover, and plain bearings being arranged between the bearing plate and the ring and between the bearing plate and the cover. This assures that the mount can be easily turned around the bearing plate.

In a further structurally simple embodiment of the invention, the horizontal shaft, which can be turned around the bearing in the stand together with the x-ray tube, the bearing housing and the mount for the cassette holders, can be locked in specific positions with a closure element which can be locked to a closure collar in one of a plurality of arrested positions. The x-ray tube can be easily set to a desired angular position in this manner.

DESCRIPTION OF THE PREFERRED EMBODIMENTS

Figure 1:
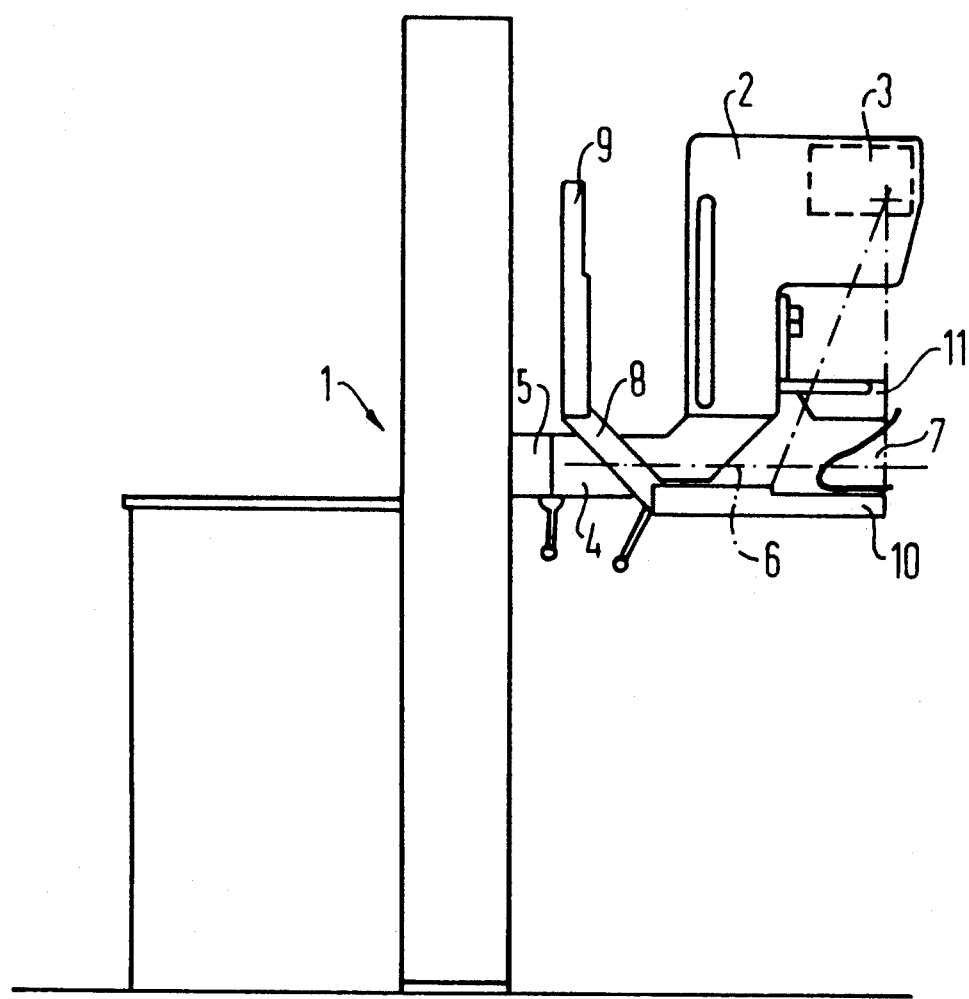
FIG. 1 is a side elevational view of an x-ray diagnostics apparatus constructed in accordance with the principles of the present invention.

A mammography apparatus constructed in accordance with the principles of the present invention is shown in FIG. 1, which includes a stand 1 having a housing 2 which contains an x-ray tube 3. The housing 2 is rotatably attached, via a horizontal shaft 4, to a bearing 5 arranged in the stand 1. The bearing 5 is vertically displaceable. The rotational center of the horizontal shaft 4 is disposed in approximate axial alignment with the center of an examination subject 7. A mount 8 for two cassette holders 9 and 10 for x-ray film cassettes of respectively different sizes is rotatably attached to the horizontal shaft 4. The cassette holders 9 and 10 are attached to the mount 8 at an angular spacing of 180°, so that when one cassette holder, such as the cassette holder 10, is in the exposure position, the other cassette holder, such as the cassette holder 9, will be situated in a standby position behind the housing 2 for the x-ray tube 3, as seen proceeding from the examination subject 7.

When an image of an examination subject 7 of a specific size is to be taken, the cassette holder which is most suitable for this size is moved from its standby position to the exposure position, with the assistance of structure described below. The rotation of the mount 8 around the shaft 4 ensues such that the cassette holders 9 and 10 each have approximately the same spacing from the rotational axis of the horizontal shaft when they are respectively situated in the exposure position.

As further shown in FIG. 1, the cassette holders 9 and 10 serve as a subject table when in the exposure position. A compression plate 11, which presses the examination subject 7 against the cassette holder 9 or 10 before an exposure is arranged at the housing 2 so as to be height-adjustable. By means of the horizontal shaft 4, the housing 2 together with the x-ray tube 3 can be rotated around the bearing 5 at the stand 1 to a different, selected exposure position. When such a rotation occurs, the mount 8 together with the cassette holders 9 and 10 are also rotated. The cassette holders 9 and 10 can also be changed from a standby position to the exposure position when the unit is in such an oblique attitude.

Figure 2:
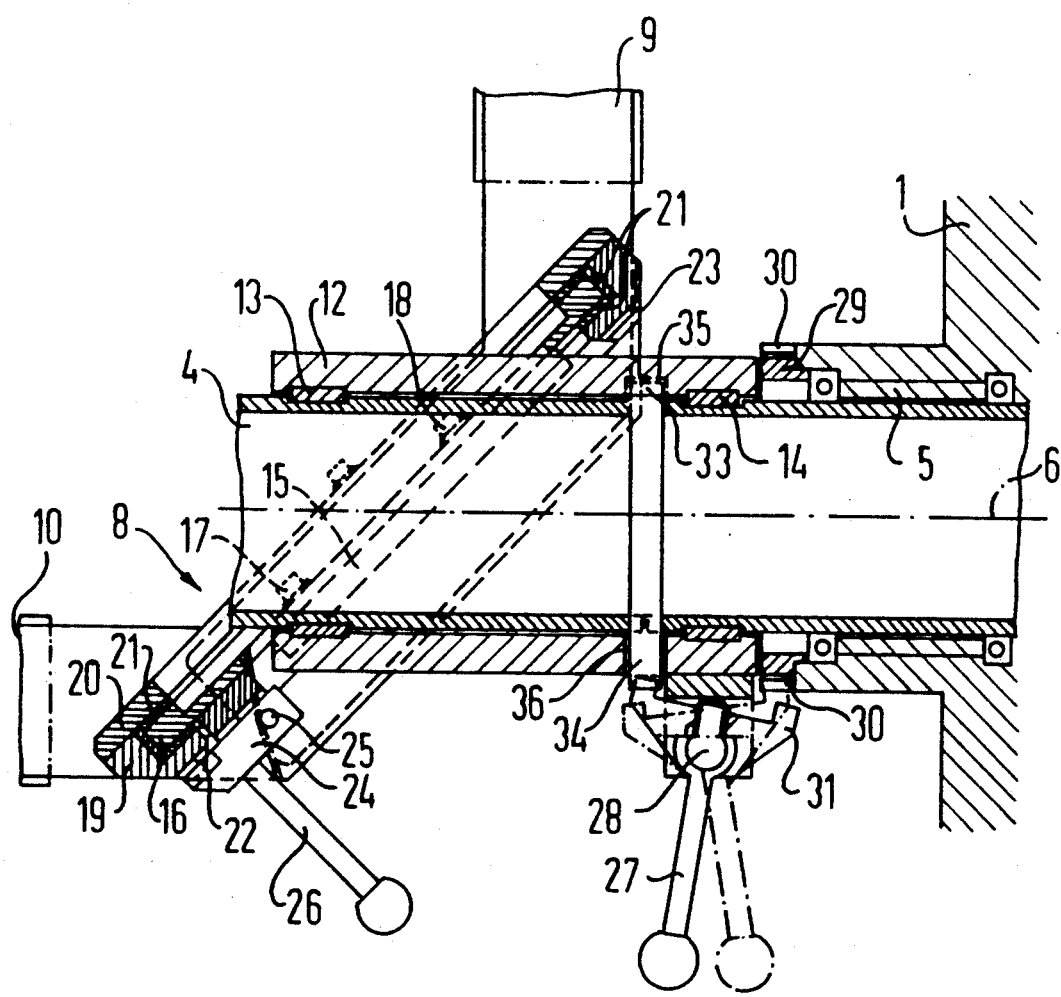
FIG. 2 is a side sectional view of the cassette position-changing arrangement in the apparatus of FIG. 1, constructed in accordance with the principles of the present invention.

The details of the rotatable attachment of the horizontal shaft 4 to the bearing 5 in the stand 1 are shown in FIG. 2. The shaft 4 is provided with a bearing housing 12 having plain bearings 13 and 14, which permit the shaft 4 to be rotated relative to the bearing housing 12. The bearing housing 12 is in turn provided with flanges 15 which are disposed at an angle of approximately 45° relative to the horizontal shaft 4, and to which a bearing plate 16 is secured with screws 17 and 18. Only one of the flanges 15 is visible in FIG. 2.

The mount 8 is provided with a ring 19 and with a cover 20 for the ring 19 which surround the bearing plate 16 around which the mount 8 is rotatable. Plain bearings 21 are provided between the bearing plate 16 and the ring 19 and between the bearing plate 16 and the cover 20, which facilitate rotation of the mount 8 around the bearing plate 16. As noted above, the cassette holders 9 and 10 are attached to the mount 8 at an angular spacing of 180°. The cover 20 is provided with respective lock channels 22 and 23 for locking the cassette holders 9 and 10 into their respective exposure positions. When one of the cassette holders 9 or 10 is brought to a desired exposure position, the lock channel, for example channel 22, will be disposed exactly in front of a closure element 24, which is rotatably attached to the bearing housing 12 by means of a shaft 25, and which can be lowered into the lock channel 22 by a lever 26. The cassette holder 10 thus is arrested in this position. When changing from one cassette holder to the other, the closure element 24 is withdrawn from the lock channel 22 with the lever 26, so that the mount 8 is rotated around the bearing plate 16 through 180° by means of the ring 19 and the cover 20 until the lock channel 23 for the cassette holder 9 resides exactly in front of the closure element 24 which, in the manner described above, arrests the cassette holder 9 in the exposure position.

As can also be seen in FIG. 2, a further lever 27, having a closure element 31, is attached to a shaft 28 so as to be rotatable around a center of the shaft 28 in the bearing housing 12. A closure collar 29, which surrounds the horizontal shaft 4, is secured in the stand 1 beyond the bearing 5. The closure collar 29 is provided with lock channels 30 which are arranged with equal angular spacing around the peripheral surface of the closure collar 29, for example at an angular spacing of 15° between each channel 30. When the lever 27 is brought to the position indicated by the dot-dashed lines in FIG. 2, i.e., when the closure element 31 is engaged into a lock channel 30, the shaft 4 is locked to the housing 2 and the x-ray tube 3 in this position. When the housing 2 together with the x-ray tube 3 and the horizontal shaft 4 are to be rotated to a selected, oblique exposure position, the closure element 31 is withdrawn from the lock channel 30 by operating the lever 27, whereupon the shaft 4 together with the housing 2 and the x-ray tube 3 can be rotated to the desired attitude. In this attitude, the shaft 4 can again be locked with the closure element 31 in the manner described above. During this rotation of the shaft 4, the bearing housing 12 and the mount 8 are also co-rotated.

As described above, the horizontal shaft 4 can also be rotated relative to the bearing housing 12. This is used in conjunction with stereotactic exposures. In such exposures, the x-ray tube 3 is rotated relative to the cassette 9 or 10 in the exposure position by an angle of approximately 3.5° on both sides of a center axis for a perpendicular exposure. In such exposures, the bearing housing 12 is locked with the closure collar 29 in the manner described above. A shaft 32 penetrates the horizontal shaft 4 perpendicularly to the rotational axis 6 of the shaft 4, and is secured in the shaft 4. The shaft 32 has opposite ends 33 and 34 which respectively proceed in channels 35 and 36. The lengths of the channels 35 and 36 are dimensioned so that the rotational movement of the shaft 4 is limited to a total of 7°. The channels 35 and 36 which are shown in FIG. 2 proceed in the direction of the plane of the drawing.

It is also possible within the context of the inventive concept disclosed herein for the mount 8 to carry three cassette holders at respective angular spacings of 120°. As a result of this angular spacing between the cassette holders, the cassette holder in their respective standby positions are not in the manner when the third cassette holder is in the exposure position.

The mount 8 is attached to the horizontal shaft 4 at an angle of 45° relative to the rotational axis 6 of the shaft 4, so that the mount 8 can be made relatively small and simple in structure while simultaneously permitting the cassette holders 9 and 10 to be movable between the exposure position and the standby position in a manner providing a non-cumbersome appearance.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray diagnostics apparatus for mammography examination of a subject comprising:
   a stand having a horizontal shaft mounted thereto for rotation around a horizontal axis, said horizontal axis being disposed in substantially axial alignment with a middle of said subject;
   an x-ray tube mounted on said horizontal shaft having a front side facing said subject and a rear side facing away from said subject;
   a plurality of x-ray film cassette holders; and
   mounting means, rotationally attached to said horizontal shaft and connected to said cassette holders, for pivoting said cassette holders respectively between an examination position and a standby position, said cassette holders being disposed relative to said mounting means so that when one of said cassette holders is in said exposure position a remainder of said cassette holders is in said standby position behind said rear of said x-ray tube proceeding from said subject, and so that each cassette holder is disposed at substantially the same distance from said horizontal axis when in said exposure position.

2. An x-ray diagnostics apparatus as claimed in claim 1 further comprising a housing attached to said horizontal shaft and containing said x-ray tube.

3. An x-ray diagnostics apparatus as claimed in claim 1 wherein said mounting means is attached to said horizontal shaft at an angle of approximately 45°.

4. An x-ray diagnostics apparatus as claimed in claim 1 wherein said plurality of cassette holders is two, and wherein said two cassette holders are disposed on said mount relative to each other at an angular spacing of 180°.

5. An x-ray diagnostics apparatus as claimed in claim 1 wherein said plurality of cassette holders is three, and wherein said three cassette holders are disposed on said mount relative to each other at an angular spacing of 120°.

6. An x-ray diagnostics apparatus as claimed in claim 1 further comprising a bearing housing attached to said horizontal shaft and containing a bearing plate attached at an angle of approximately 45° relative to said horizontal shaft, said mounting means being attached to said bearing plate.

7. An x-ray diagnostics apparatus as claimed in claim 6 wherein said bearing housing has at least one flange to which said bearing plate is attached.

8. An x-ray diagnostics apparatus as claimed in claim 6 wherein said mounting means is attached so as to be rotatable around said bearing plate with a ring and a ring cover, and further comprising plain bearings disposed between said bearing plate and said ring and between said bearing plate and said ring cover.

9. An x-ray diagnostics apparatus as claimed in claim 8 further comprising a user-manipulable closure element, and a plurality of lock channels in said ring engageable with said closure element, said lock channels being positioned relative to said cassette holders so that when a lock channel engages said closure element one of said cassette holders is arrested in said exposure position.

10. An x-ray diagnostics apparatus as claimed in claim 8 further comprising a user-manipulable closure element, and a plurality of lock channels in said ring cover engageable with said closure element, said lock channels being positioned relative to said cassette holders so that when a lock channel engages said closure element one of said cassette holders is arrested in said exposure position.

11. An x-ray diagnostics apparatus as claimed in claim 6 wherein said horizontal shaft, said x-ray tube, said bearing housing and said mounting means are co-rotatable around said horizontal axis, and further comprising means for arresting said horizontal shaft, said x-ray tube, said bearing housing and said mount in combination at a selected angular position around said horizontal axis.

12. An x-ray diagnostics apparatus as claimed in claim 11 wherein said means for arresting comprises a closure collar having a plurality of arresting positions respectively corresponding to angular positions of said combination, and a user-manipulable closure element engageable with said closure collar in a selected one of said arresting positions.

13. An x-ray diagnostics apparatus as claimed in claim 12 wherein said closure collar surrounds said horizontal shaft and is secured to said stand, and wherein said closure element is attached to said horizontal shaft.

14. An x-ray diagnostics apparatus for mammography examination of a subject comprising:
   a stand having a horizontal shaft mounted thereto for rotation around a horizontal axis, said horizontal axis being disposed in substantially axial alignment with a middle of said subject;
   an x-ray tube mounted on said horizontal shaft having a front side facing said subject and a rear side facing away from said subject;
   a plurality of x-ray file cassette holders; and
   mounting means, rotationally attached to said horizontal shaft at an angle of approximately 45° relative to said horizontal axis and connected to said cassette holders, for pivoting said cassette holders around said horizontal axis respectively between an exposure position and a standby position, said cassette holders being attached to said mounting means so as to form an angle of approximately 90° relative to each other so that when one of said cassette holders in said exposure position a remainder of said cassette holders is in said standby position behind said rear of said x-ray tube proceeding from said subject, and so that each cassette holder is disposed at substantially the same distance from said horizontal axis when in said exposure position.

15. An x-ray diagnostics apparatus as claimed in claim 14 further comprising means for arresting rotation of said mounting means around said horizontal axis at selected angular locations to lock a selected one of said cassette holders in said exposure position.

16. An x-ray diagnostics apparatus as claimed in claim 14 further comprising means for arresting rotation of said horizontal shaft around said horizontal axis to lock said x-ray tube in a selected angular position around said horizontal axis.

* * * * *